US005714157A

United States Patent [19]
Sandell et al.

[11] Patent Number: 5,714,157
[45] Date of Patent: Feb. 3, 1998

[54] WATER-DISPERSIBLE GRANULAR AGRICULTURAL COMPOSITIONS MADE BY HEAT EXTRUSION

[75] Inventors: Lionel Samuel Sandell; Robert David Wysong, both of Wilmington, Del.

[73] Assignee: E. I. Du Pont de Nemours and Company, Wilmington, Del.

[21] Appl. No.: 617,862

[22] PCT Filed: Aug. 29, 1994

[86] PCT No.: PCT/US94/09632

§ 371 Date: Mar. 20, 1996

§ 102(e) Date: Mar. 20, 1996

[87] PCT Pub. No.: WO95/08265

PCT Pub. Date: Mar. 30, 1995

Related U.S. Application Data

[63] Continuation-in-part of Ser. No. 125,895, Sep. 23, 1993, abandoned.

[51] Int. Cl.$^6$ .................................................... A01N 25/12
[52] U.S. Cl. .................... 424/409; 424/405; 424/408; 424/419; 504/116; 71/DIG. 1
[58] Field of Search .................. 504/116, 212, 504/214; 71/DIG. 1; 424/405, 406, 408, 409, 410, 419, 421

[56] References Cited

U.S. PATENT DOCUMENTS 5,100,667   3/1992   Chan et al. .............................. 424/405

FOREIGN PATENT DOCUMENTS

WO 90/12503   11/1990   WIPO .
WO 92/15197    9/1992   WIPO .

*Primary Examiner*—Neil S. Levy

[57] ABSTRACT

Rapidly disintegrating water-dispersible granular agricultural compositions comprising by weight based on the total weight of the composition (a) 0.01–80% of one or more active ingredients, (b) 0.004–60% of a base, (c) 5–95% of urea, (d) 1–30% of one or more urea modifiers and (e) optionally one or more additives selected from wetting agents, dispersants, lubricants, anti-caking agents, chemical stabilizers, and inert diluents that are formed by extrusion.

10 Claims, No Drawings

WATER-DISPERSIBLE GRANULAR AGRICULTURAL COMPOSITIONS MADE BY HEAT EXTRUSION

This application is a 371 application of PCT/US94/09632 filed Aug. 29, 1994, which is a continuation-in-part of U.S. Ser. No. 125,895, filed Sep. 23, 1993 now abandoned.

BACKGROUND OF THE INVENTION

The present invention pertains to rapidly disintegrating water-dispersible granular compositions comprising active ingredients of value in agriculture.

Water-dispersible granular compositions are becoming increasingly popular in agriculture. Accordingly, it is advantageous to discover improved compositions and methods of production. Most granulation methods in current use, generally referred to herein as wet granulation, require introduction of water for granulation and then a drying step to remove the water. The drying step is expensive, time-consuming and may create dust, and it would be advantageous if granulation could be accomplished without water.

The granular agricultural compositions are most commonly applied by diluting an effective dose with water in a mix tank and spraying the locus to be treated. An important feature of the granules is the rate at which they will disintegrate in the spray water to form the final dispersion or solution. Faster disintegration rates are preferred.

World Patent WO 92/15197 discloses water-dispersible granular compositions of agricultural active ingredients which were made by heat extrusion. Granulation is accomplished by the fusion of heat-sensitive components; no water is added and no drying step is required. A limitation of the granular compositions of this art though is that they require incorporation of effervescence in order to disintegrate in water as rapidly as granular compositions made by wet granulation. The problem with effervescent ingredients is that they are very sensitive to moisture and tend to react prematurely during manufacture and storage. Extra precautions in handling must be taken, and shelf-life may be limited.

The present invention is an improvement in the prior art by the selection of ingredients which yield noneffervescent granular compositions made by heat extrusion having superior disintegration rate and improved shelf-life.

SUMMARY OF THE INVENTION

The invention is a rapidly disintegrating water dispersible granular composition for agricultural applications. The composition comprises by weight based on the total weight of the composition:

(a) 0.01–80% of one or more agriculturally active ingredient (b) 0–60% of a base (c) 5–95% of urea (d) 1–30% of one or more urea modifier, and (e) optionally one or more additives selected from the group consisting of wetting agents, dispersants, lubricants, anti-caking agents, chemical stabilizers and inert diluents, the sum of all ingredients totaling 100%.

Preferably the active ingredient is 0.03–70%, the urea is 7–75% and the urea modifier is 3–15%.

More preferably the active ingredient is 10–65% and the urea is 10–65%.

Another embodiment of the invention is a process for preparing a rapidly disintegrating water dispersable granular agricultural composition comprising (a) extruding a dry premix through a die or a screen at elevated temperatures, preferably below 115° C., said premix comprising the composition described above, and (b) cutting, breaking, or sieving the extruded strands to form granules.

The active ingredient is at least one pesticide or a chemical used for crop protection. Especially advantageous compositions comprise a mixture of two active ingredients. More specifically, ingredients are selected from the class of herbicides, fungicides, bactericides, insecticides, insect antifeedants, acaricides, miticides, nematocides, and plant growth regulants.

The addition of base is preferred when the composition comprises an acidic active ingredient that becomes water soluble as a salt. Examples of acidic actives of this sort are glyphosate, 2,4-D and the sulfonylurea class of herbicides. Levels of base include up to a 2:1 mole ratio of a base to salt-forming active ingredient, preferably a mole ratio range from 0.4:1 to 1.6:1, and most preferred a mole ratio range from 0.8:1 to 1.2:1. In any case, the mount of base will generally not exceed 60% of the composition. Suitable bases include but are not limited to alkali metal and alkaline earth metal oxides, hydroxides, phosphates, hydrogen phosphates, silicates, benzoates and borates. The phosphates are preferred.

We term the species of (d) above "urea modifier" because in combination with the urea in (c) there is formed a novel extrusion aid which allows extrusion to take place at temperatures much below the melting point of pure urea (132° C.). Extrusion temperatures are preferably below 115° C.

DETAILED DESCRIPTION OF THE INVENTION

In recent years formulations based on water-dispersible granules have become increasingly popular because they offer several advantages over other types of agricultural formulations. They are more stable during storage and transport than aqueous suspension concentrates which can settle. They are convenient to handle and measure and are relatively dust-free in comparison to wettable powders. And they avoid the toxicity, environmental and odor problems associated with solvent-based formulations such as emulsion concentrates and organic suspension concentrates.

To make water-dispersible granules useful for application they are usually diluted in a mix tank containing water to make a solution or dispersion which can be sprayed. The dispersed particles should be no larger than 50μ in their largest dimension to avoid nozzle pluggage or premature settling which results in uneven application of the pesticide. It is therefore necessary that the granular composition rapidly and completely disintegrates in the dilution water. We refer to all granular compositions of the present invention as water-dispersible even though they may be totally water-soluble when diluted.

Conventional wet granulation methods for preparing water-dispersible granule compositions involve (1) water-spraying in fluidized bed or pan granulation equipment, (2) spray-drying, (3) extrusion of a water-wet paste, and (4) dry compaction. Granules prepared by fluid-bed, spray-drying or pan granulation use water in the granulation step which must be removed later; however, such granules will generally disintegrate rapidly when diluted in water. Dry compaction of noneffervescent compositions and paste extrusion generally do not produce rapidly disintegrating granules, and paste extrusion also requires a drying step.

The present invention comprises noneffervescent water-dispersible granular compositions and a process of extruding dry premixes of these compositions through a die or screen at elevated temperature and chopping, sieving or breaking the extruded material to form granular compositions that disintegrate rapidly in water.

In the process of this invention, the components of the composition are combined to form a premix which may be blended to obtain a homogeneous mixture. The premix may be also milled to reduce the average particle size, or alternatively, milling of components may be done separately prior to incorporation into the premix.

The premix is fed or metered to an extruder which has been heated by conventional means such as electrical resistance or steam. Suitable extruders include single and twin-screw models, and roll-type extrusion presses (radial extruders). Twin-screw extruders are preferred. In some types of extrusion equipment, for example, a California Pellet Mill, the heat can be generated from friction. Other means of heating the premix include preheating the premix before extrusion, or heating the individual components of the premix before blending. It may be desirable to separately feed some individual components to the extruder rather than incorporate them in the premix.

The extruder is heated and maintained at an appropriate temperature profile for a particular composition. Typically there are several heating zones along an extruder barrel which will be set at different temperatures, ranging from about 20° C. at the feed throat up to 130° C. at the zone of maximum temperature, preferably to a maximum of 115° C. The appropriate temperature profile along the barrel will vary with the composition, and can be determined readily by one skilled in the art. High temperatures which can cause decomposition of the active ingredient and the urea should be avoided.

The heated premix is extruded through a die or screen. Compositions which give even melt flow through the die holes are preferred. The die holes range in diameter from 0.25 mm to 7 mm, preferably from 0.5 mm to 3 mm. Depending on the composition and the type of extruder used, the extruded material might be recycled until the strands are uniform in texture. Generally the extruded material is allowed to cool to harden and reduce tack, although this may not be necessary. Compositions which harden quickly without tack are preferred since they may be more easily cut into granules. The extruded strands are chopped, sieved or rolled and then screened to give granules. In some cases the strands may be sufficiently brittle to break on their own into short lengths.

The compositions of this invention comprise: (a) one or more agricultural active ingredient; (b) urea; (c) one or more urea modifier in water-soluble form selected from the group organosulfonate salts and alcohol ethoxylates; and, (d) optionally, one or more other additives.

Agricultural active ingredients include herbicides, fungicides, bacteriacites, insecticides, insect antifeedants, acaricites, miticides, nematocides, and plant growth regulants. The active ingredient may be water-soluble or water-insoluble and should be chemically stable in the extrusion temperature range. It is preferred that the melting point of the active ingredient is above the extrusion temperature; lower melting active ingredients may be used but they may require a carrier. Examples of suitable active ingredients include the following: Herbicides such as acifluorfen, asulam, atrazine, bensulfuron methyl, bentazon, bromacil, bromoxynil, hydroxybenzonitrile, chloramben, chlorimuron ethyl, chloroxuron, chlorsulfuron, chlortoluron, cyanazine, dazomet, desmediphan, dicamba, dichlorbenil, dichlorprop, diphenamid, dipropetryn, diuron, thiameturon, fenac, renuton, fluometuron, fluridone, fomesafen, glyphosate, hexazinone, imazamethabenz, imazaquin, imazethapyr, ioxynil, isoproturon, isouron, isoxaben, karbutilate, lenacil, MCPA, MCPB, mefenacet, mefluidide, methabenzthiauron, methazole, metribuzin, metsulfuron methyl, monuron, naptalam, neburon, nitralin, norflurzaon, oryzalin, perfluidone, phenmedipham, picloram, prometryn, pronamide, propanil, propazine, pyrazon, rimsulfuron, siduron, simazine, sulfometuron methyl, tebuthiuron, terbacil, terbuthylazine, terbutryn, thifensulfuron methyl, triclopyr, 2,4-D, 2,4-DB, triasulfuron, wibenuron methyl, triflusulfuron, primisulfuron, pyrazosulfuron ethyl, nicosulfuron, ethametsulfuron methyl, 2-[2,4-dichloro-5-[(2-propynyl)oxy]phenyl-5,6,7,8-tetrahydro-1,2,4-triazolo-[4,3-a]-pyridin-3-(H)-one, methyl 2-[[[[(4,6-dimethoxy-2-pyrimidinyl)amino]carbonyl]amino]sulfonyl]-6-(trifluoromethyl)-3-pyridinecarboxylate sodium salt, N-[(4,6-dimethoxypyrimidin-2-yl)aminocarbonyl]-1-methyl-4-(2-methyl-2H-tetrazol-5-yl)-1H-pyrazole-5-sulfonamide and N-[(4,6-dimethoxypyrimidin-2-yl)aminocarbonyl]-1-methyl-4-ethoxycarbonyl-5-pyrazolesulfonamide; fungicides such as carbendazim, thiuram, riodine, chloroneb, captan, folpot, thiophanatemethyl, thiabendazole, chlorothalonil, dichloran, captafol, iprodione, vinclozolin, kasugamycin, triadimenol, flutriafol, flusilazol, hexaconazole, and fenarimol; bactericides such as oxytetracycline dihydrate; acaricides such as hexathizox, oxythioquinox, dienochlor, and cyhexatin; and insecticides such as carbofuran, carbaryl, thiodicarb, deltamethrin, and tetrachlorvinphos. Active ingredient also include the salts of the active ingredients.

When the active ingredient is substantially water-insoluble, a) it must have a melting or softening point above the extrusion temperature, or b) it must be supported by a carrier with a melting or softening point above the extrusion temperature. Otherwise the active ingredient will smear and disperse poorly when the final product is diluted in a spray tank.

Preferred combinations of active ingredients include metsulfuron methyl with one or more of the following: chlorimuron ethyl; bensulfuron methyl; propanil; MCPA; 2,4-D; glyphosate; triasulfuron. Further preferred combinations include bensulfuron methyl with one or more of the following: propanil; mefenacet; N-[(4,6-dimethoxypyrimidin-2-yl) aminocarbonyl]-1-methyl-4-ethoxycarbonyl-5-pyrazolesulfonamide; N-[(4,6-dimethoxypyrimidin-2-yl) aminocarbonyl]-1-methyl-4-(2-methyl-2H-tetrazol-5-yl)-1H-pyrazole-5-sulfonamide. Most preferred are metsulfuron methyl and bensulfuron methyl.

In a preferred embodiment of the present invention, the active ingredient and any optional additives are water-soluble thus making the final granular composition water-soluble. Water-soluble granular compositions are advantageous because the premix does not generally require a separate milling step thus saving time and expense. Also, granular compositions which are completely or mostly water-soluble tend to disintegrate more rapidly than granular compositions which contain higher mounts of water-insoluble components.

Another preferred embodiment of the present invention is the inclusion of base in the composition when a poorly water-soluble active ingredient will become more water-soluble in the presence of said base. Examples of active ingredients which will become more soluble in the presence of base include glyphosate, 2,4-D, bromoxanil and the sulfonyl urea class of herbicides. Especially preferred are the sulfonylurea herbicides which is meant to include the entire class of herbicides containing the following and any closely related chemical functionalities:

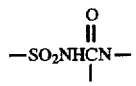

Suitable bases include but are not limited to alkali metals and alkaline earth metals of the following: oxides, hydroxides, phosphates, hydrogen phosphates, silicates, benzoates and borates. The phosphates are preferred and the di and tribasic sodium and potassium phosphates are most preferred. Useful levels of base include up to a 2:1 mole ratio relative to acidic active ingredient. Ammonium and alkali metal carbonate and bicarbonate species are less preferred because of the potential for gas evolution ($NH_3$ and $CO_2$) during extrusion at elevated temperatures.

The compositions of the present invention contain a novel extrusion aid which is a combination of urea and urea-modifier. The materials used as urea modifiers are well known to function as wetting and dispersing agents in agricultural formulations. We have found surprisingly that their combination with urea provides a novel extrusion aid which allows the extrusion process of the present invention to proceed at temperatures much lower than the melting point of urea alone (132° C.). Molten urea itself is not a useful extrusion aid, and extrusion at temperatures approaching the melting point of urea is not preferred.

Urea-modifiers include the following organosulfonate salts: (a) benzene sulfonates and alkyl-substituted benzene sulfonates; (b) alkyl α-olefin sulfonates; (c) naphthalene sulfonates and alkyl-substituted naphthalene sulfonates; and (e) condensates of (c) with formaldehyde. More specifically, alkyl-substituted benzene sulfonates includes mono-, di- and tri-substituted derivatives where alkyl is $C_1$ to $C_{20}$ for mono-substitution and $C_1$ to $C_6$ for di- and tri-substitution; alkyl α-olefin sulfonates includes alkyl of $C_{10}$ to $C_{20}$; and, alkyl-substituted naphthalene sulfonates includes mono-, di- and tri-substituted derivatives where alkyl is $C_1$ to $C_6$. The associated cations may be any agricultural suitable cation rendering the organosulfonate water-soluble; preferred are sodium and ammonium. Preferred organosulfonate urea-modifiers are sodium and ammonium alkyl naphthalene sulfonates, sodium and ammonium alkyl naphthalene sulfonate formaldehyde condensates, and mixtures of the foregoing.

We speculate that under heat and pressure a eutectic mixture forms between urea and the organosulfonate urea-modifiers. The softening point of the eutectic is lower than that of any of the components. Eutectic formation was not found to be dependent on residual moisture levels.

Urea-modifiers also include alcohol ethoxylates derived from $C_6$ to $C_{20}$ linear alcohols ethoxylated with 3 to 20 moles of ethylene oxide. The preferred HLB range is 8 to 17. Most preferred are linear alcohol ethoxylates containing an average of 8 to 14 alcohol carbon atoms and 3 to 10 ethylene oxide units. Commercial linear alcohol ethoxylates contain a certain percentage of branched species. Preferably the percent linear species is greater than 85% and more preferably greater than 90%. The source of alcohol ethoxylates with the highest percent linear content known to us at this time is the Alfonic® series from Vista Chemical.

We speculate that the alcohol ethoxylate urea-modifiers (liquids or soft pastes at room temperature) form a clathrate complex with urea. The complex can be formed by (1) spraying, blending and shearing the alcohol ethoxylate (heated if necessary) into pulverized urea in a separate step, or (2) spraying, blending and shearing the alcohol ethoxylate (heated if necessary) directly into the urea-containing pre-mix. A suitable blender for such a procedure would be a Littleford mixer. The clathrate not only functions as an extrusion aid, it also appears to improve uniformity of flow through the die and enhance the rate at which the extruded strands become brittle thereby facilitating strand cutting at the die face. In a preferred embodiment compositions contain both organosulfonate and linear alcohol ethoxylate urea-modifiers.

The advantage of the urea-based extrusion aid of the present invention over the thermoplastic polymers such as polyethoxylated dinonylphenol used in prior art is that the present extrusion aid is more rapidly soluble in water, thus providing final granular compositions which disintegrate rapidly in water without the need for effervesence or other disintegration aids.

The compositions of this invention may optionally include additives such as wetting agents and dispersants other than those used as urea modifiers, lubricants, anti-caking agents, chemical stabilizers and diluents. One skilled in the art would understand the purpose and selection of these additives.

Wetting agents include but are not limited to alkyl sulfosuccinates, laurares, alkyl sulfate and phosphate esters, acetylenic diols, ethoxyfluorinated alcohols, ethoxylated silicones and alkyl phenol ethoxylates, as well as the organic sulfonates and alcohol ethoxylates used as urea modifiers. If additional wetting agent is needed, useful levels include up to about 5% by weight.

Dispersants include but are not linked to sodium, calcium and ammonium salts of ligninsulfonates (optionally polyethoxylated); sodium and ammonium salts of maleic anhydride copolymers and sodium salts of condensed phenolsulfonic acid as well as the napthalene sulfonate-formaldehyde condensates used as urea modifiers. If additional dispersant is needed, useful levels include up to about 10% by weight.

Lubricants include but are not limited to polyvinylpyrrolidone, polyvinylalcohol and polyethylene oxide. They have a median molecular weight greater than 50,000, a melt flow temperature of at least 98° C., and do not behave as surfactants. Polyethylene oxide is preferred. If lubricant is needed, levels up to about 3% by weight may be included in the composition. Higher levels are less desirable because they tend to slow the disintegration rate of the granule.

Anticaking agents to prevent clumping of granules stored under hot warehouse conditions include but are not limited to sodium and ammonium phosphates, sodium acetate, sodium metasilicate, magnesium, zinc and calcium sulfates, magnesium hydroxide, (all optionally as hydrates), anhydrous calcium chloride, molecular sieves, sodium alkylsulfosuccinates, calcium and barium oxides. If anticaking agent is needed, useful levels include up to about 10% by weight.

Chemical stabilizers to prevent decomposition of active ingredient during storage include but are not limited to sulfates of alkaline earths and transition metals such as magnesium, zinc, aluminum and iron; lithium, sodium and potassium phosphates; calcium chloride and oxide; and, boric anhydride. If chemical stabilizer is needed, useful levels include up to about 10% by weight.

Diluents may be water-soluble or water-insoluble. The water-soluble diluents may be salts, surfactants or carbohydrates which dissolve rapidly in water; non-limiting examples include sulfates of sodium, potassium, magnesium and zinc, sodium and potassium chloride, sorbitol, sodium benzoate, lactose, and alkali metal and alkali earth phosphates. Water-insoluble diluents include but are not limited to clays, synthetic and diatomaceous silicas, calcium and magnesium silicates, titanium dioxide, aluminum, calcium and zinc oxide, calcium and magnesium carbonate, sodium, potassium, calcium and barium sulfate, and charcoal. Water-soluble diluents are preferred. If diluent is needed, levels up to about 60% by weight may be included.

Advantages of the noneffervescent heat-extruded granular compositions of the present invention include (1) rapid disintegration ha water, (2) good resistance to caking, (3) uniform size and bulk density, (4) good attrition resistance, (5) a simple method of production which is nonaqueous and requires no drying step, and (6) good processability and shelf life due to the lack of effervescent components.

The rate of granule disintegration is measured in a glass tube assembly measuring 30.5 cm in length with a 40 mm inside diameter. The glass robe is cut ha the center to produce two 15.25 cm halves. One end of each half is sealed. The other end is left open and ground flat. A groove is cut into the open end of both halves to accomodate a Viton "O" ring with an outer diameter of 6 cm. The bottom half of the assembly is filled with 90 mL of deionized water and 0.5 g of granules are placed on a semi-circular 20 mesh screen positioned over the open end of the lower tube. (Alternatively, the granules may be added directly to the water in the lower tube). The "O" ring is placed in the groove on the open end of the lower half. The grooved end of the upper half is then positioned over the "O" ring and the assembly is clamped together water-tight, using a glass pipe clamp. The sealed assembly is attached in the center to a "Roto-Torque" heavy duty rotator (Cole-Parmer Instrument Co.). It is then rotated end-over-end at 6 rpm until the sample has completely disintegrated ha the water. The time from the start of rotation (or addition of the sample directly to the water) to completion of the disintegration is recorded. Disintegration times of less than 150 seconds are preferred, more preferably less than 120 seconds. For disintegration in cold water (e.g. 40° C.) longer times, up to 5 minutes, are acceptable.

The caking resistance is determined by the following procedure. A stainless steel disc (0.9 mm thick×51 mm diameter) is fit flush with the bottom of a glass cylinder (75 mm long with a 46.5 mm inside diameter and 51 mm outside diameter) and held in place with tape; the sample of granular composition (20 g) is delivered to the cylinder assembly, resting on the bottom disc; the sample is leveled, and a second stainless steel disc (0.9 mm thick×44.5 mm diameter) is placed on the top of the granules. A 400 g weight (45 mm diameter or less) is placed on top of the upper disc and the entire assembly is placed in an oven at 54° C. and left undisturbed for 1 week. Then, the assembly is removed from the oven, the weight is removed, and the sample is allowed to cool to room temperature. The bottom disc is then detached from the cylinder with a minimum amount of agititation to the sample; if the sample flows freely out of the cylinder, the resistance to caking is deemed excellent; if the sample remains in the cylinder, the cake is removed, placed onto a flat surface and a penetrometer is used with a single-edged razor to measure the minimum force necessary to cleave the cake. Compositions with cakes requiring a force of less than 100 g are acceptable; preferably less than 5 g force is required. Most preferred is a composition which is free flowing after the test period.

The bulk density of a granular composition will affect the rate of dispersion, with higher bulk densities yielding slower disintegration times for a given composition. The "untapped" bulk density is measured in a 50 cc or 100 cc graduated cylinder.

The attrition as determined by the method in U.S. Pat. No. 3,920,442 (Col. 8, lines 548). The test is modified to use test samples of the commercial granule size (e.g., 74–2,000µ). Attrition values of less than 40% are acceptable; values less than 30% are preferred.

The following examples are presented to illustrate, but not to restrict, this invention.

| Identity of Ingredients Used in Examples | |
|---|---|
| Name | Identity |
| Lomar ® PW (Henkel Corp) | Sodium naphthalene sulfonate formaldehyde condensate (now known as Emery 5353) |
| Morwet ® EFW (Witco Corp) | Mixture of sodium alkyl naphthalene sulfonates and alkyl carboxylate |
| Alkanol ® XC (DuPont Co.) | Sodium alkyl naphthalene sulfonate |
| Siponate ® DS-10 (Rhone-Poulenc Co) | Sodium dodecyl benzene sulfonate |
| Siponate ® 301-10F (Rhone-Poulenc Co) | Sodium alkyl alpha-olefin sulfonate |
| Tamol ® SN (Rohm and Haas Co) | Sodium naphthalene sulfonate formaldehyde condensate |
| Polyox ® WSR N-750 (Union Carbide Corp) | Polyethylene oxide |
| Alfonic ® 1412-60 (Vista Chemical Co) | Linear alcohol ethoxylate $CH_3(CH_2)_xCH_2(OCH_2CH_2)_nOH$, where $x = 10$–$12$; $n = 7$ avg. |

EXAMPLE 1

This example illustrates a fast-dispersing extrudable composition containing a naphthalene sulfonate condensate and alkyl napthalene sulfonate as urea modifiers. The composition contains a base, dibasic potassium phosphate, at approximately a 1:1 mole ratio to the acidic active, metsulfuron methyl.

A 500 g premix was formulated from the ingredients listed below. The ingredients were blended and then passed through a MikroPulverizer hammer mill. The milled premix was slowly added to a 1 inch Wayne single screw extruder with a 24:1 L/D barrel using a screw with a 3:1 compression ratio. The extruder had three electrical heating zones along the barrel plus a band heater for the die. A mechanical or electronic pressure indicator was fitted near the end of the barrel to measure hydraulic pressures dose to the die. A temperature probe was also located near the .end of the barrel to measure the temperature of the melt just before the die.

The premix was extruded through a die containing eight 0.9 mm diameter holes arranged in a circular pattern. The extruded product was allowed to cool for a few minutes then it was chopped up in a small food processor and screened to obtain the 14 to 20 U.S. sieve cut size.

| | Wt % |
|---|---|
| PREMIX FORMULATION | |
| Metsulfuron methyl technical | 22.0 |
| Lomar ® PW | 5.0 |
| Morwet ® EFW | 3.0 |
| $K_2HPO_4$ | 10.0 |
| Urea | 60.0 |

|  | Wt % |
|---|---|
| EXTRUSION CONDITIONS | |
| Extrusion temperature ranges (°C.) | |
| zone 1 (feed zone) | 31–32 |
| zone 2 | 55–59 |
| zone 3 | 87–88 |
| die | 90–92 |
| Hydraulic pressure range ($10^6$ Pa) | 1.4–10.7 |
| Melt temperature (°C.) | 99–101 |
| PROPERTIES OF GRANULES: | |
| Average disintegration time (seconds) | 24, granules dissolved |
| Caking (g force) | none, free flow |
| Bulk Density (g/cc) | 0.45 |

EXAMPLES 2–3

These examples illustrate the effect of adding small amounts of high molecular weight polyethylene oxide as a lubricant to the formulation. 300 g of each premix was prepared and extruded using the procedure described in Example 1.

|  | Ex. 2 Wt % | Ex. 3 Wt % |
|---|---|---|
| Metsulfuron methyl technical | 22.0 | 22.0 |
| Lomar ® PW | 5.0 | 5.0 |
| Morwet ® EFW | 3.0 | 3.0 |
| K₂HPO₄ | 10.0 | 10.0 |
| Polyox ® WSR-N750 | 0.5 | 1.0 |
| Urea | 59.5 | 59.0 |
| EXTRUSION CONDITIONS | | |
| Extrusion Temp Ranges (°C.): | | |
| Zone 1 | 30–33 | 30–34 |
| Zone 2 | 56–59 | 55–58 |
| Zone 3 | 85–86 | 82–84 |
| Die | 90–91 | 85–88 |
| Hydraulic Pressure Range ($10^6$ Pa) | 1.6–18.3 | 4.7–31.2 |
| Melt Temperature (°C.) | 99–100 | 99–100 |
| PROPERTIES OF GRANULES: | | |
| Average disintegration time (seconds) | 39 | 52 |
| Caking (g force) | none free flow | none free flow |
| Bulk density (g/cc) | 0.50 | 0.46 |

The strands extruded in Examples 2 and 3 were smoother than those of Example 1, with breakup times increasing with increasing polyethylene oxide content. The granules of both examples dissolved completely.

EXAMPLE 4

This example illustrates the use of a different alkyl napthalene sulfonate, Alkanol® XC. The procedure of Example 2 was followed.

|  | Wt % |
|---|---|
| PREMIX FORMULATION | |
| Metsulfuron methyl technical | 22.0 |
| Lomar ® PW | 5.0 |
| Alkanol ® XC | 3.0 |
| K₂HPO₄ | 10.0 |
| Urea | 60.0 |
| EXTRUSION CONDITIONS | |
| Extrusion temperature ranges (°C.): | |
| zone 1 (feed zone) | 28–30 |
| zone 2 | 52–58 |
| zone 3 | 85–87 |
| die | 89–91 |
| Hydraulic pressure range ($10^6$ Pa) | 4.6–17.8 |
| Melt temperature (°C.) | 99–101 |
| PROPERTIES OF GRANULES: | |
| Average disintegration time (seconds) | 33, granules dissolved |
| Caking (g force) | none, free flow |
| Bulk Density (g/cc) | 0.51 |

EXAMPLE 5

This example illustrates a lower level of alkyl napthalene sulfonate. The procedure of Example 1 was used except the premix was milled differently. The premix was prepared using hammermilled technical and granulated urea. 150 g of premix was milled in 5×5 second bursts in a Tekmar model A20 blender-type mill.

|  | Wt % |
|---|---|
| PREMIX FORMULATION | |
| Metsulfuron methyl technical | 22.0 |
| Lomar ® PW | 5.0 |
| Alkanol ® XC | 1.0 |
| K₂HPO₄ | 10.0 |
| Urea | 62.0 |
| EXTRUSION CONDITIONS | |
| Extrusion temperature ranges (°C.): | |
| zone 1 (feed zone) | 30 |
| zone 2 | 55–57 |
| zone 3 | 87–89 |
| die | 89–91 |
| Hydraulic pressure range ($10^6$ Pa) | 10.0–50.4 |
| Melt temperature (°C.) | 99–101 |
| PROPERTIES OF GRANULES: | |
| Average disintegration time (seconds) | 46, granules dissolved |
| Bulk Density (g/cc) | 0.56 |

EXAMPLE 6

This example illustrates the use of a different napthalene sulfonate condensate, Tamol® SN. The procedure of Example 2 was followed.

|  | Wt % |
|---|---|
| PREMIX FORMULATION | |
| Metsulfuron methyl technical | 22.0 |
| Tamol ® SN | 5.0 |
| Alkanol ® XC | 3.0 |
| K₂HPO₄ | 10.0 |
| Urea | 60.0 |

-continued

| | Wt % |
|---|---|
| EXTRUSION CONDITIONS | |
| Extrusion temperature ranges (°C.): | |
| zone 1 (feed zone) | 29–30 |
| zone 2 | 57–58 |
| zone 3 | 85–86 |
| die | 89–91 |
| Hydraulic pressure range ($10^6$ Pa) | 1.8–11.6 |
| Melt temperature (°C.) | 98–99 |
| PROPERTIES OF GRANULES: | |
| Average breakup time (sec) | 21, granules dissolved |
| Caking (g force) | none, free flow |
| Bulk Density (g/cc) | 0.50 |

EXAMPLE 7

This example illustrates a composition containing a linear alcohol ethoxylate preblended with a portion of the urea in a ratio of 1 part Alfonic® 1412-60 to 4 parts urea. The premix was prepared as described for Example 5.

| | Wt % |
|---|---|
| PREMIX FORMULATION | |
| Metsulfuron methyl technical | 22.0 |
| Lomar ® PW | 5.0 |
| 1:4 Alfonic ® 1412-60/urea preblend | 15.0 |
| Alkanol ® XC | 3.0 |
| $K_2HPO_4$ | 10.0 |
| Urea | 45.0 |
| EXTRUSION CONDITIONS | |
| Extrusion temperature ranges (°C.): | |
| zone 1 (feed zone) | 31–32 |
| zone 2 | 55–58 |
| zone 3 | 83–84 |
| die | 84–86 |
| Hydraulic pressure range ($10^6$ Pa) | 3.9–26.3 |
| Melt temperature (°C.) | 96–98 |
| PROPERTIES OF GRANULES: | |
| Average disintegration time (seconds) | 39, granules dissolved |
| Caking (g force) | <19, partial cake only |
| Bulk Density (g/cc) | 0.61 |

EXAMPLE 8

This example illustrates a composition containing an alkyl benzene sulfonate, Siponate® DS-10, as a secondary urea modifier. The premix was prepared as described for Example 5.

| | Wt % |
|---|---|
| PREMIX FORMULATION | |
| Metsulfuron methyl technical | 22.0 |
| Lomar ® PW | 5.0 |
| Alkanol ® XC | 3.0 |
| $K_2HPO_4$ | 10.0 |
| Siponate ® DS-10 | 2.0 |
| Urea | 58.0 |

-continued

| | Wt % |
|---|---|
| EXTRUSION CONDITIONS | |
| Extrusion temperature ranges (°C.): | |
| zone 1 (feed zone) | 29–30 |
| zone 2 | 56–59 |
| zone 3 | 87–88 |
| die | 90–91 |
| Hydraulic pressure range ($10^6$ Pa) | 3.9–15.9 |
| Melt temperature (°C.) | 100–101 |
| PROPERTIES OF GRANULES: | |
| Average disintegration time (seconds) | 39, granules dissolved |
| Caking (g force) | none, free flow |
| Bulk Density (g/cc) | 0.45 |

EXAMPLE 9

This example illustrates a composition containing an alkyl alpha-olefin sulfonate, Siponate® 301-10P, as a secondary urea modifier. The premix was prepared as described for Example 5.

| | Wt % |
|---|---|
| PREMIX FORMULATION | |
| Metsulfuron methyl technical | 22.0 |
| Lomar ® PW | 5.0 |
| Alkanol ® XC | 3.0 |
| $K_2HPO_4$ | 10.0 |
| Siponate ® 301-10P | 2.0 |
| Urea | 58.0 |
| EXTRUSION CONDITIONS | |
| Extrusion temperature ranges (°C.): | |
| zone 1 (feed zone) | 28–29 |
| zone 2 | 53 |
| zone 3 | 87 |
| die | 91–92 |
| Hydraulic pressure range ($10^6$ Pa) | 2.4–12.2 |
| Melt temperature (°C.) | 100–102 |
| PROPERTIES OF GRANULES: | |
| Average disintegration time (seconds) | 24, granules dissolved |
| Caking (g force) (1 week/54° C.) | <19, partial cake only |
| Bulk Density (g/cc) | 0.48 |

EXAMPLE 10

This example illustrates a composition containing basic components comprised of dibasic potassium phosphate and calcium oxide. The total base-to-active mole ratio is 2:1. Premix was prepared by the procedure of Example 5.

| | Wt % |
|---|---|
| PREMIX FORMULATION | |
| Metsulfuron methyl technical | 22.0 |
| Lomar ® PW | 5.0 |
| Morwet ® EFW | 3.0 |
| $K_2HPO_4$ | 10.0 |
| Polyox ® WSR-N750 | 0.5 |
| Calcium oxide | 3.0 |
| Urea | 56.0 |

-continued

| | Wt % |
|---|---|
| EXTRUSION CONDITIONS | |
| Extrusion temperature ranges (°C.): | |
| zone 1 (feed zone) | 28–29 |
| zone 2 | 55–58 |
| zone 3 | 85–86 |
| die | 88–91 |
| Hydraulic pressure range ($10^6$ Pa) | 0.41–6.5 |
| Melt temperature (°C.) | 100–101 |
| PROPERTIES OF GRANULES: | |
| Average disintegration time (seconds) | 57, for 3/4 of the sample. About 1/4 of the sample stuck to the glass walls of the apparatus |
| Caking (g force) | none, free flow |
| Bulk Density (g/cc) | 0.53 |

EXAMPLE 11

This example illustrates a composition containing potassium chloride as a water-soluble diluent. The premix was prepared by the procedure of Example 5.

| | Wt % |
|---|---|
| PREMIX FORMULATION | |
| Metsulfuron methyl technical | 22.0 |
| Lomar ® PW | 5.0 |
| 1:4 Alfonic ® 1412-60/urea preblend | 25.0 |
| $K_2HPO_4$ | 10.0 |
| KCl | 19.0 |
| Urea | 18.5 |
| Cabosil ® | 0.5 |
| Extrusion temperature ranges (°C.): | |
| zone 1 (feed zone) | 32–34 |
| zone 2 | 55–57 |
| zone 3 | 86 |
| die | 89–92 |
| Hydraulic pressure range ($10^6$ Pa) | 2.3–17.2 |
| Melt temperature (°C.) | 99–101 |
| PROPERTIES OF GRANULES: | |
| Average disintegration time (seconds) | 52, granules dissolved |
| Caking (gms force) | <19, partial cake only |
| Bulk Density (g/cc) | 0.62 |

EXAMPLE 12

This example illustrates a composition containing potassium sulfate as a water soluble diluent. The premix was prepared by the procedure of Example 5.

| | Wt % |
|---|---|
| PREMIX FORMULATION | |
| Metsulfuron methyl technical | 22.0 |
| Lomar ® PW | 5.0 |
| 1:4 Alfonic ® 1412-60/urea preblend | 25.0 |
| $K_2HPO_4$ | 10.0 |
| $K_2SO_4$ | 19.0 |
| Urea | 18.5 |
| Cabosil ® | 0.5 |
| Extrusion temperature ranges (°C.): | |
| zone 1 (feed zone) | 33–35 |
| zone 2 | 55–56 |
| zone 3 | 85–87 |
| die | 89–91 |
| Hydraulic pressure range ($10^6$ Pa) | 2.3–9.5 |
| Melt temperature (°C.) | 100 |
| PROPERTIES OF GRANULES: | |
| Average disintegration time (seconds) | 55, granules dissolved |
| Caking (g force) | 63, partial cake only |
| Bulk Density (g/cc) | 0.64 |

EXAMPLE 13

This example illustrates a composition containing 52% metsulfuron methyl technical. The base, dipotassium phosphate, is at a 1:1 mole ratio with the active.

| | Wt % |
|---|---|
| PREMIX FORMULATION | |
| Metsulfuron methyl technical | 52.0 |
| Lomar ® PW | 5.0 |
| Morwet ® EFW | 3.0 |
| 1:4 Alfonic ® 1412-60/urea preblend | 17.1 |
| $K_2HPO_4$ | 22.9 |
| EXTRUSION CONDITIONS | |
| Extrusion temperature ranges (°C.): | |
| zone 1 (feed zone) | 32 |
| zone 2 | 55 |
| zone 3 | 85 |
| die | 92–97 |
| Hydraulic pressure range ($10^6$ Pa) | 2.2–31.6 |
| Melt temperature (°C.) | 106–111 |
| PROPERTIES OF GRANULES: | |
| Average disintegration time (seconds) | 115, granules dissolved |
| Caking (g force) | 150, partial cake only |
| Bulk Density (g/cc) | 0.61 |

EXAMPLE 14

This example illustrates thifensulfuron methyl as active ingredient with >1 molar ratio of $K_3PO_4$ as base.

| | Wt % |
|---|---|
| PREMIX FORMULATION | |
| Thifensulfuron methyl technical | 52.0 |
| Lomar ® PW | 5.0 |
| 1:4 Alfonic ® 1412-60/urea preblend | 25.0 |
| $K_3PO_4$ | 18.0 |
| EXTRUSION CONDITIONS | |
| Extrusion temperature ranges (°C.): | |
| zone 1 (feed zone) | 71 |
| zone 2 | 87 |
| zone 3 | 104 |
| die | 95 |
| Hydraulic pressure range ($10^6$ Pa) | 6.2 |
| Melt temperature (°C.) | 100 |

| | Wt % |
|---|---|
| PROPERTIES OF GRANULES: | |
| Average disintegration time (seconds) | 90 |
| Caking (g force) | — |
| Bulk Density (g/cc) | — |

EXAMPLE 15

This example illustrates tribenuron methyl as active ingredient with $K_3PO_4$/CaO as base. CaO also improves chemical stability of active ingredient.

| | Wt % |
|---|---|
| PREMIX FORMULATION | |
| Tribenuron methyl technical | 52.0 |
| Lomar ® PW | 5.0 |
| 1:4 Alfonic ® 1412-60/urea preblend | 25.0 |
| $K_3PO_4$ | 3.5 |
| CaO | 7.5 |
| Urea | 7.0 |
| EXTRUSION CONDITIONS | |
| Extrusion temperature ranges (°C.): | |
| zone 1 (feed zone) | — |
| zone 2 | — |
| zone 3 | — |
| die | — |
| Hydraulic pressure range ($10^6$ Pa) | 2.0 |
| Melt temperature (°C.) | 76 |
| PROPERTIES OF GRANULES: | |
| Average disintegration time (seconds) | 72 |
| Caking (g force) | — |
| Bulk Density (g/cc) | — |

EXAMPLE 16

This example illustrates glyphosate as active ingredient in combination with metsulfuron methyl.

| | Wt % |
|---|---|
| PREMIX FORMULATION | |
| Glyphosate, sodium salt (technical) | 36.0 |
| Metsulfuron methyl technical | 1.0 |
| Lomar ® PW | 5.0 |
| 1:4 Alfonic ® 1412-60/urea preblend | 25.0 |
| $K_2HPO_4$ | 1.0 |
| CaO | 5.0 |
| Extrusion temperature ranges (°C.): | |
| zone 1 (feed zone) | — |
| zone 2 | — |
| zone 3 | — |
| die | — |
| Hydraulic pressure range ($10^6$ Pa) | 4.7 |
| Melt temperature (°C.) | 87 |
| PROPERTIES OF GRANULES: | |
| Average disintegration time (seconds) | 72 |
| Caking (g force) | — |
| Bulk Density (g/cc) | — |

EXAMPLE 17

This example illustrates hexazinone as active ingredient. Shows water soluble formulation without use of base.

| | Wt % |
|---|---|
| PREMIX FORMULATION | |
| Hexazinone technical | 52.0 |
| Lomar ® PW | 5.0 |
| 1:4 Alfonic ® 1412-60/urea preblend | 25.0 |
| Urea | 18.0 |
| EXTRUSION CONDITIONS | |
| Extrusion temperature ranges (°C.): | |
| zone 1 (feed zone) | 45 |
| zone 2 | 64 |
| zone 3 | 79 |
| die | 80 |
| Hydraulic pressure range ($10^6$ Pa) | 6.1 |
| Melt temperature (°C.) | 80 |
| PROPERTIES OF GRANULES: | |
| Average disintegration time (seconds) | 62 |
| Caking (g force) | — |
| Bulk Density (g/cc) | — |

EXAMPLE 18

This example illustrates Diuron as active ingredient. Demonstrates rapid dispersion without base.

| | Wt % |
|---|---|
| PREMIX FORMULATION | |
| Diuron technical | 62.0 |
| Lomar ® PW | 5.0 |
| 1:4 Alfonic ® 1412-60/urea preblend | 25.0 |
| KCl | 8.0 |
| Extrusion temperature ranges (°C.): | |
| zone 1 (feed zone) | 57 |
| zone 2 | 74 |
| zone 3 | 88 |
| die | — |
| Hydraulic pressure range ($10^6$ Pa) | 1.5 |
| Melt temperature (°C.) | 86 |
| PROPERTIES OF GRANULES: | |
| Average disintegration time (seconds) | 60 |
| Caking (g force) | — |
| Bulk Density (g/cc) | — |

EXAMPLE 19

This example illustrates metsulfuron methyl extrusion where no organosulfonate is used—only linear alcohol ethoxylate.

| | Wt % |
|---|---|
| PREMIX FORMULATION | |
| Metsulfuron methyl technical | 22.0 |
| 1:3 Alfonic ® 1412-60/urea preblend | 50.0 |
| $K_2HPO_4$ | 10.0 |
| Urea | 18.0 |
| Extension temperature ranges (°C.): | |
| zone 1 (feed zone) | 72 |
| zone 2 | 80 |
| zone 3 | 93 |
| die | 95 |
| Hydraulic pressure range ($10^6$ Pa) | 10.0 |
| Melt temperature (°C.) | 97 |

EXAMPLE 20

This example illustrates a chemically stable extrusion of 2,4-D/tribenuron methyl combination.

| | Wt % |
|---|---|
| PREMIX FORMULATION | |
| Tribenuron methyl technical | 2.1 |
| 2,4D | 52.0 |
| Lomar ® PW | 4.0 |
| 1:4 Alfonic ® 1412-60/urea preblend | 20.0 |
| K₃PO₄ | 5.0 |
| Urea | 16.9 |
| EXTRUSION CONDITIONS | |
| Extrusion temperature ranges (°C.): | |
| zone 1 (feed zone) | 42 |
| zone 2 | 75 |
| zone 3 | 77 |
| die | 77 |
| Hydraulic pressure range (10⁶ Pa) | 4.7 |
| Melt temperature (°C.) | 76 |
| PROPERTIES OF GRANULES: | |
| Average disintegration time (seconds) | 55 |
| Caking (g force) | — |
| Bulk Density (g/cc) | — |

EXAMPLE 21

This example illustrates a chemically stable extrusion of 2,4-D/tribenuron methyl combination.

| | Wt % |
|---|---|
| PREMIX FORMULATION | |
| Tribenuron methyl technical | 2.1 |
| 2,4D | 52.0 |
| Lomar ® PW | 4.0 |
| 1:4 Alfonic ® 1412-60/urea preblend | 20.0 |
| K₃PO₄ | 5.0 |
| KCl | 16.9 |
| EXTRUSION CONDITIONS | |
| Extrusion temperature ranges (°C.): | |
| zone 1 (feed zone) | — |
| zone 2 | — |
| zone 3 | — |
| die | — |
| Hydraulic pressure range (10⁶ Pa) | 13.1 |
| Melt temperature (°C.) | 71 |
| PROPERTIES OF GRANULES: | |
| Average disintegration time (seconds) | 45 |
| Caking (g force) | — |
| Bulk Density (g/cc) | — |

EXAMPLE 22

This example illustrates triflusulfuron as active ingredient. Uses linear alcohol ethoxylate as only urea modifier. Also illustrates rapid dispersion without use of a base.

| | Wt % |
|---|---|
| PREMIX FORMULATION | |
| Triflusulfuron technical | 52.0 |
| Lomar ® PW | 5.0 |
| 1:4 Alfonic ® 1412-60 /urea preblend | 25.0 |
| KCl | 18.0 |
| EXTRUSION CONDITIONS | |
| Extrusion temperature ranges (°C.): | |
| zone 1 (feed zone) | 49 |
| zone 2 | 68 |
| zone 3 | 76 |
| die | 79 |
| Hydraulic pressure range (10⁶ Pa) | — |
| Melt temperature (°C.) | 79 |
| PROPERTIES OF GRANULES: | |
| Average disintegration time (seconds) | 64 |
| Caking (g force) | — |
| Bulk Density (g/cc) | — |

EXAMPLE 23

This example illustrates 2-[2,4-dichlor-5-[(2-propynyl)oxy}phenyl-5,6,7,8-tetrahydro-1,2,4-triazolo-[4,3-a]-pyridin-3-3(H)-one as active ingredient. Also same dispersion illustration as Example 23.

| | Wt % |
|---|---|
| PREMIX FORMULATION | |
| 2-[2,4-dichlor-5-[(2-propynyl)oxy}phenyl-5,6,7,8-tetrahydro-1,2,4-triazolo-[4,3-a]-pyridin-3-3(H)-one | 62.0 |
| Morwet ® D425 | 5.0 |
| Morwet ® EFW | 8.0 |
| 1:4 Alfonic ® 1412-60/urea preblend | 15.0 |
| KCl | 10.0 |
| EXTRUSION CONDITIONS | |
| Extrusion temperature ranges (°C.): | |
| zone 1 (feed zone) | 48 |
| zone 2 | 77 |
| zone 3 | 87 |
| die | 89 |
| Hydraulic pressure range (10⁶ Pa) | 4.1 |
| Melt temperature (°C.) | 86 |
| PROPERTIES OF GRANULES: | |
| Average disintegration time (seconds) | 120 |
| Caking (g force) | — |
| Bulk Density (g/cc) | — |

EXAMPLE 24

This example illustrates chlorimuron ethyl/metsulfuron methyl as active ingredient combination.

| | Wt % |
|---|---|
| PREMIX FORMULATION | |
| Metsulfuron methyl technical | 26.0 |
| Chlorimuron ethyl technical | 26.0 |
| Lomar ® PW | 4.0 |
| 1:4 Alfonic ® 1412-60/urea preblend | 20.0 |

-continued

|  | Wt % |
|---|---|
| $K_3PO_4$ | 15.0 |
| KCl | 9.0 |
| EXTRUSION CONDITIONS | |
| Extrusion temperature ranges (°C.): | |
| zone 1 (feed zone) | 93 |
| zone 2 | 94 |
| zone 3 | 93 |
| die | 90 |
| Hydraulic pressure range ($10^6$ Pa) | 18.6 |
| Melt temperature (°C.) | 90 |
| PROPERTIES OF GRANULES: | |
| Average disintegration time (seconds) | 120 |
| Caking (g force) | — |
| Bulk Density (g/cc) | — |

EXAMPLE 25

This example illustrates triflusulfuron as active ingredient.

|  | Wt % |
|---|---|
| PREMIX FORMULATION | |
| Triflusulfuron technical | 52.0 |
| Lomar ® PW | 4.0 |
| 1:4 Alfonic ® 1412-60 urea/preblend | 20.0 |
| $Na_2SiO_3$ | 15.0 |
| KCl | 9.0 |
| EXTRUSION CONDITIONS | |
| Extrusion temperature ranges (°C.): | |
| zone 1 (feed zone) | 42 |
| zone 2 | 48 |
| zone 3 | 66 |
| die | 69 |
| Hydraulic pressure range ($10^6$ Pa) | 15.2 |
| Melt temperature (°C.) | 69 |
| PROPERTIES OF GRANULES: | |
| Average disintegration time (seconds) | 115 |
| Caking (g force) | — |
| Bulk Density (g/cc) | — |

EXAMPLES 26–28 and COMPARISON EXAMPLES A–C

The same procedure was used for all of following examples. In each case, 300 gm of formulation was weighed up and milled in a small, high speed lab mill (IKA Universal M20) for 5 bursts of 5 seconds each. The premix was then hand-blended by rolling in a jar for 3 minutes. It was then added to a small KayIron® feeder which fed the powder into a Prism Engineering 16 mm twin screw extruder. The extruder was equipped with a 15:1 L/D ratio twin screw assembly inside a barrel with 2 heating zones. The feed throat of the barrel whew the powder entered the extruder was water-cooled. A die with a single 1.5 mm diameter diehole was fitted to the end of the barrel and was heated separately with a band heater. Screw speed was 100 rpm. Barrel and die set point temperatures, melt pressures and melt temperatures were as indicated below. The extruded strands were chopped up in a mini-food processor and sifted on a stack of 10 and 20 mesh U.S. sieves. Granules in the −10 mesh/+20 mesh size range were collected and used to determined the disintegration rate. These granules are larger than those used in examples hereinbefore, consequently the disintegration times are longer.

Comparison Example A was carded out as set forth in Example 5 of WO 92/15197 except that the effervescent agents, citric acid (1.0%) and sodium bicarbonate (1.5%), are removed, the water-soluble diluent, sorbitol, is increased by 2.5% to make up the difference and the extruder was the 1 inch extruder of present Example 1. Example A is compared to Example 26, which is the formulation of Example 13 hereinbefore described. Comparison Example B was carded out as set forth in Example 5 of WO 92/15197 except that the 1 inch extruder of present Example 1 was used, the metsulfuron methyl was reduced (from 52.0 to 22.0%), the effervescent agents removed, substituting therefor increased water-soluble diluent which was changed from sorbitol to urea. Example B is compared to Example 27, which the formulation of Example 4 hereinbefore described. It can be seen that the present compositions provide superior disintegration rate relative to non-effervescence, heat-extruded prior art compositions.

|  | 26 | A | 27 | B |
|---|---|---|---|---|
| PREMIX FORMULATION | | | | |
| Metsulfuron methyl technical | 52.0 | 52.0 | 22.0 | 22.0 |
| Lomar ® PWA |  | 7.0 |  | 7.0 |
| Lomar ® PW | 5.0 |  | 5.0 |  |
| Pluronic ® F108 |  | 8.0 |  | 8.0 |
| 1:4 Alfonic 1412-60/urea preblend | 17.1 |  |  |  |
| Morwet ® EFW | 3.0 |  |  |  |
| $K_2HPO_4$ | 22.9 |  | 10.0 |  |
| Polyplasdone ® XL-10 |  | 2.0 |  | 2.0 |
| Alkanol ® XC |  | 3.0 |  |  |
| Urea |  |  | 60.0 | 61.0 |
| Sorbitol |  | 31.0 |  |  |
| EXTRUSION CONDITIONS | | | | |
| Extrusion temperature ranges (°C.): | | | | |
| Zone 1 (feed zone) | 67–74 | 58–69 | 67–74 | 67–73 |
| Zone 2 | 95–97 | 71–96 | 94–96 | 96–97 |
| Die | 97–99 | 71–98 | 96–99 | 97–99 |
| Hydraulic pressure range ($10^6$ Pa) | 1.0–3.4 | 1.4–2.3 | 1.4–1.7 | 2.2–3.4 |
| PROPERTIES OF GRANULES | | | | |
| Average disintegration time (seconds) | 1' 58" | 4' 46" | 1' 48" | 3' 25" |

The formulation for Comparison Example C was carried out as set forth in Example 1 of WO 92/15197. Example C is compared to Example 28 which is the formulation of Example 18 hereinbefore described. Again, the superior disintegration rate of the present composition relative to the non-effervescent heat-extruded prior art composition is shown.

|  | (Wt %) | |
|---|---|---|
|  | 28 | C |
| PREMIX FORMULATION | | |
| Diuron technical | 62.0 | 62.4 |
| Lomar ® PW | 5.0 | 10.0 |
| 1:4 Alfonic ® 1412-60/urea preblend | 25.0 |  |
| KCl | 8.0 |  |
| Macol ® DNP150 |  | 5.0 |
| Morwet ® EFW |  | 2.0 |
| Polyplasdone ® XL-10 |  | 2.0 |

-continued

|  | (Wt %) | |
|---|---|---|
|  | 28 | C |
| Urea | | 18.6 |
| EXTRUSION CONDITIONS | | |
| Extrusion temperature ranges (°C.): | | |
| Zone 1 (feed zone) | 78–88 | 88 |
| Zone 2 | 90–95 | 90–91 |
| Die | 90–95 | 90–91 |
| Hydraulic pressure range ($10^6$ Pa) | 1.7–3.3 | 1.6–3.6 |
| PROPERTIES OF GRANULES | | |
| Average disintegration time (seconds) | 54 | 200 |

EXAMPLE 29

This example illustrates the use of a dome granulator normally used for paste extrusion. The following premix, 200 grams, was prepared as in Example 5 of the present specification.

|  | Wt. % |
|---|---|
| Rimsulfuron | 52 |
| $K_3PO_4$ | 17 |
| Emery 5353 | 10 |
| Urea | 21 |

Employing a Fuji Paudal Co., Ltd. dome granulator model DG-L1 equipped with a 50 mm diameter feed screw and a 1.0 mm thick dome having multiple 1.0 mm diameter holes, the premix, preheated to 70° C., was fed to the charge hopper and the dome, hopper, barrel, and screw of the extruder were preheated to about 80° C. using a hot air gun. At screw speeds of 35 rpm and above, a steady state of extrusion was reached where external heating was eliminated and the frictional shear on the premix between the end wiper flight of the screw and the inside of the dome maintained the melt extrusion. An extrudate was obtained which was similar to that obtained from the single- or twin-screw melt extruders. It was cooled and chopped as in previous examples and was found to dissolve completely in water in 57 seconds.

What is claimed:

1. Rapidly disintegrating water dispersible granular agricultural compositions which disperse in water to form particles no greater than 50 microns consisting of by weight based on the total weight of the composition, (a) 0.01–80% of one or more active ingredients selected from herbicides, insecticides and fungicides which are poorly water soluble having melting points above or below the extrusion temperature and which when water soluble have melting points above the extrusion temperature, (b) 0.004–60% of a base which renders the poorly soluble active ingredient water-soluble as a salt, (c) 5–95% of urea, (d) 1–30% of one or more urea modifiers which when mixed with urea allow the extrusion process to proceed at temperatures much lower than the melting point of urea alone, (e) 0–10% of one or more additives selected from the group consisting of wetting agents, dispersants, lubricants, anticaking agents and chemical stabilizers, and (f) 0–60% of inert diluents the sum of all ingredients totaling 100%.

2. The composition of claim 1 where the active ingredient is 0.03–70%, the urea is 7–75%, and the urea modifier is 3–15%.

3. The composition of claim I where the active ingredient is 10–65% and the urea is 10–65%.

4. The composition of claim 1 wherein there is one active ingredient, a sulfonylurea herbicide characterized by the chemical functionality

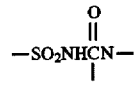

5. The composition of claim 4 wherein the active ingredient is metsulfuron methyl.

6. The composition of claim 1 wherein the active ingredients are metsulfuron methyl and bensulfuron methyl.

7. The composition of claim 1 wherein the active ingredient is water-soluble, the urea modifier is sodium salts of naphthalene sulfonates.

8. The composition of claim 3 wherein the base is 1–20%.

9. The composition of claim 5 wherein the base is 1–20%.

10. A process for preparing a rapidly disintegrating water-dispersible granular composition comprising (a) extruding the composition of claim 1 through a die or a screen at elevated temperatures and (b) cutting, breaking or sieving the extruded strands to form granules.

* * * * *